United States Patent
Kunz et al.

(10) Patent No.: US 6,742,399 B2
(45) Date of Patent: Jun. 1, 2004

(54) RESPIRATORY FLOW SENSOR WITH FLOW CHANNEL HAVING A MEASURING TRANSDUCER AND AIR RESISTANCE BODY

(75) Inventors: Rainer Kunz, Lübeck (DE); Götz Kullik, Lübeck (DE); Dieter Engel, Reinfeld (DE); Thomas Leyer, Lübeck (DE)

(73) Assignee: Dräger Medizintechnik GmbH, Lubeck (DE)

( * ) Notice: Subject to any disclaimer, the term of this patent is extended or adjusted under 35 U.S.C. 154(b) by 0 days.

(21) Appl. No.: 09/846,623

(22) Filed: May 1, 2001

(65) Prior Publication Data

US 2002/0007685 A1 Jan. 24, 2002

(30) Foreign Application Priority Data

Jul. 19, 2000 (DE) ......................................... 100 35 054

(51) Int. Cl.[7] ................................................. G01F 1/37
(52) U.S. Cl. .................................. 73/861.52; 73/861.55
(58) Field of Search ....................... 73/861.57, 861.58, 73/861.22, 861.63, 861.52, 861.55; 128/725, 204.23

(56) References Cited

U.S. PATENT DOCUMENTS

| | | | |
|---|---|---|---|
| 4,015,473 A | * | 4/1977 | Kleuters et al. ............... 73/205 |
| 4,047,521 A | * | 9/1977 | Kramer et al. ............ 73/211 X |
| 5,379,650 A | * | 1/1995 | Kofoed et al. ........... 73/861.52 |
| 5,925,831 A | * | 7/1999 | Storsved ................... 73/861.52 |

FOREIGN PATENT DOCUMENTS

DE      196 17 318 A1      11/1997

* cited by examiner

Primary Examiner—Harshad Patel
(74) Attorney, Agent, or Firm—McGlew and Tuttle, P.C.

(57) ABSTRACT

A respiratory flow sensor, which is suitable for use near a patient, covers a broad gas volume flow measuring range with a low breathing flow resistance and good, reproducible measured signal quality at the same time. The respiratory flow sensor has a first air resistance body (3) with a blunt end and with an opposite pointed end. The air resistance body (3) is arranged between the measuring transducer (5), of which there is at least one, and the patient-side end (P) of the respiratory flow sensor. The pointed end of the first air resistance body (3) points toward the measuring transducer (5). A second air resistance body (4) with a pointed end is arranged between the measuring transducer (5), of which there is at least one, and the end of the respiratory flow sensor that is away from the patient. The pointed end of the second air resistance body (4) also points toward the measuring transducer (5).

20 Claims, 2 Drawing Sheets

RESPIRATORY FLOW SENSOR WITH FLOW CHANNEL HAVING A MEASURING TRANSDUCER AND AIR RESISTANCE BODY

FIELD OF THE INVENTION

The present invention pertains to a respiratory flow sensor with at least one measuring transducer for the breathing gas volume flow and with at least one air resistance body in a common flow channel.

BACKGROUND OF THE INVENTION

A respiratory flow sensor described in DE 196 17 318 A1 has an air resistance body arranged in a flow channel and two measuring transducers designed as temperature sensors. This prior-art device is characterized in that the inflow and outflow areas of the flow channel are provided with a grid each and with a corresponding scattering surface, which is separated therefrom in space. As a result, the flow profile in the flow channel is smoothed and better measurement results may be obtained at the same time for the gas volume flow ("flow") from and/or to the patient.

Even though the measuring transducers used hitherto for respiratory flow measurements are suitable, in principle, for gas volume flow measurements, the measured signal depends strongly on the nonuniform profile of the flow velocity in the flow cross section of the flow channel, especially in the case of hot wire and differential pressure measuring transducers, because greatly different incoming flow conditions with correspondingly different degrees of turbulence may occur in the case of use of a respiratory flow sensor near the patient depending on whether the respiratory flow is from or to the patient and depending on the geometric conditions upstream and downstream of the measuring transducer.

The prior-art possibility of making the flow uniform along a shorter section by means of fine-mesh screens installed in the flow channel with and without scattering surface is linked with the drawbacks of an undesired additional pressure loss and the risk of clogging of the meshes of the screen by condensate drops or sputum.

SUMMARY AND OBJECTS OF THE INVENTION

To overcome the drawbacks of the prior-art arrangement, the object of the present invention is to provide a respiratory flow sensor, which is suitable especially for use near a patient, which covers a broad gas volume flow measuring range, which has a low respiratory flow resistance at the same time and which has a good, reproducible measured signal quality.

According to the invention, a respiratory flow sensor is provided with at least one measuring transducer for the breathing gas volume flow and with at least one air resistance body in a common flow channel. An air resistance body is provided with a blunt end and with an opposite, pointed end. The air resistance body is arranged between the measuring transducer (of which there is at least one) and a patient-side end of the respiratory flow sensor. The pointed end of the air resistance body points toward the measuring transducer.

The solution is particularly suitable for making the flow profile of the gas volume flow exhaled by the patient uniform and for measuring both the inhaled and the exhaled gas volume flows.

A second air resistance body with a pointed end may be arranged between the measuring transducer (of which there is at least one) and the end of the respiratory flow sensor, which end is away from the patient. The pointed end of the second air resistance body also points toward the measuring transducer.

The respiratory flow sensor may be made in one piece with a patient adapter with two legs. The two legs may be pivotable around an axis of rotation and the axis of rotation may be arranged at right angles to the central longitudinal axis of the flow channel. The respiratory flow sensor may have a T-shaped adapter connect to the legs.

The flow channel may narrow from both ends to the measuring transducer (of which there is at least one). The measuring transducer (of which there is at least one), sends a measured signal that is proportional to the breathing gas volume flow flowing through the flow channel. The measuring transducer (of which there is at least one) is selected from the group of ultrasonic, hot wire or differential pressure measuring transducers with or without movable diaphragms.

The first and/or the second air resistance bodies may have a rotationally symmetrical design. A symmetry axis of the air resistance bodies may be made to coincide with the central longitudinal axis of the flow channel. The blunt end of the first air resistance body may have a base in the form of a circle or a regular polygon. Following the pointed end, the second air resistance body first has a cylindrical course with a closure joining it in the form of a rounded truncated cone. A chamfer or a rounding may be provided between the base and the jacket surface of the first air resistance body. A plug may extend essentially in parallel to the central longitudinal axis of the flow channel. The plug may be used to lead out the measured signals of the measuring transducer (of which there is at least one). The distance between the measuring transducer (of which there is at least one) and each of the air resistance bodies may correspond at least to the diameter of the respective air resistance body. The respiratory flow sensor may be equipped with optical windows arranged opposite and in parallel to the central longitudinal axis for spectroscopic radiation through the flow channel and with a breathing gas sampling channel.

A substantial advantage of the respiratory flow sensor according to the present invention is that a gas volume flow measuring range from about 1 L per minute to about 120 L per minute can be covered at a required respiratory flow resistance of about 3.0 mbar at a gas volume flow of 60 L per minute and with a reproducible measured signal quality. The result can be attributed to the special design of the respiratory flow sensor with one or preferably two special air resistance bodies in front of and behind the measuring transducer, of which there is at least one, which air resistance bodies lead to an extensive smoothing of the flow profile in the flow channel for the gas volume flow measuring range. If this smoothing of the flow profile was not performed, different measurement results are obtained for the same gas volume flow depending on the position of the respiration tube connected to the respiratory flow sensor and depending on the position and the size of the particular endotracheal catheter being used.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
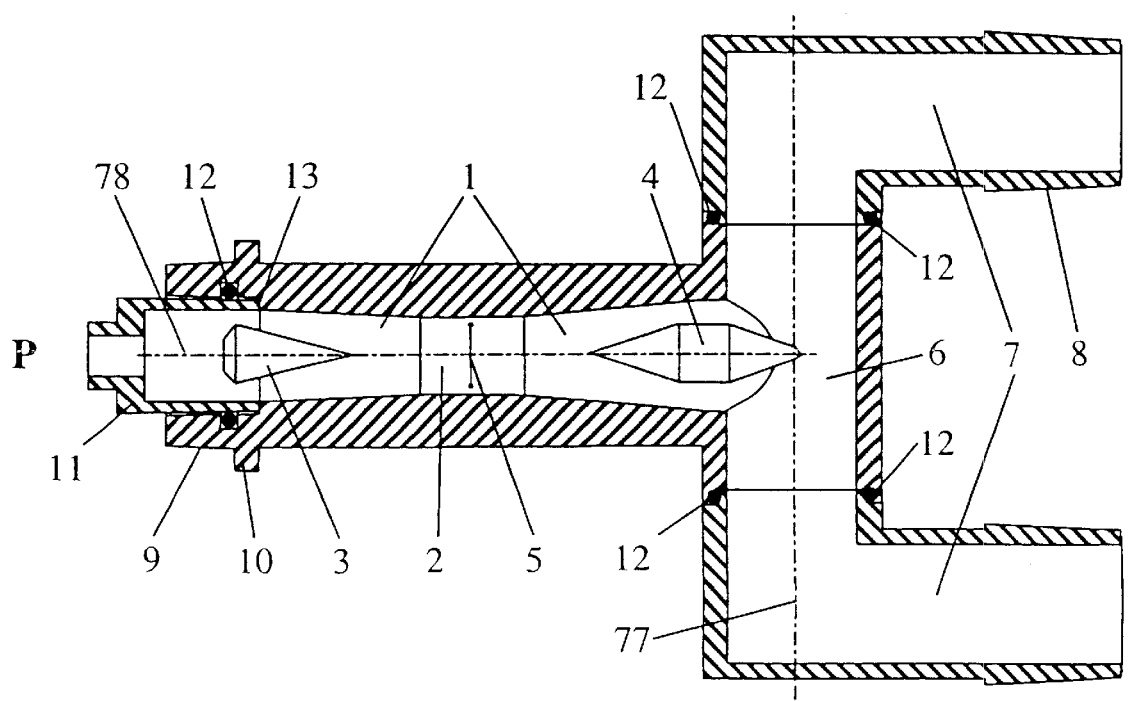
FIG. 1 is a sectional view through a respiratory flow sensor according to the present invention with a T-shaped adapter and two rotatable legs and FIG. 2 is a detail view of a respiratory flow sensor according to the present invention according to FIG. 1 with additional elements.

Referring to the drawings in particular, the medical respiratory flow sensor according to FIG. 1 comprises a flow channel 1, which narrows continuously from both sides, namely, from the patient side P and the opposite side, to the measuring cross section 2. The air resistance bodies 3, 4 are used to make the flow uniform. The at least one measuring transducer 5 in the measuring cross section 2 is shown in the example as a hot wire. The flow channel 1 is joined by a T-shaped adapter 6 with two legs 7, which are used to connect breathing tubes (inhalation line and exhalation line). The flow channel 1, the T-shaped adapter 6 and the legs 7 are pivotable around the axis of rotation 77 with seals 12. This arrangement replaces a conventional plug-in combination of a so-called Y-piece without measuring function and a hitherto unknown respiratory flow sensor near the patient. The connection between the connected breathing tubes and the patient-side connection is substantially shortened by this design according to the present invention.

The air resistance bodies 3, 4 are preferably rotationally symmetrical in relation to the central longitudinal axis 78 of the respiratory flow sensor. The air resistance bodies 3, 4 are arranged between the measuring transducer 5 (of which there is at least one) and the patient-side end P, on the one hand, and between the measuring transducer 5 (of which there is at least one) and the opposite end of the respiratory flow sensor away from the patient.

The air resistance bodies 3, 4 have a pointed end and a blunt end, and the pointed end points toward the at least one measuring transducer 5 in the measuring cross section.

To obtain good results, it was found that the distance between the pointed end of the air resistance bodies 3, 4 and the measuring transducer 5 (of which there is at least one) should correspond at least to the diameter of the respective air resistance body 3, 4. The smoothing and the uniformization of the flow is brought about by the flow arriving at the blunt end of the air resistance bodies 3, 4 being more or less deflected. Thus, the breathing gas flow exhaled by the patient P, arriving from the left, reaches the blunt end of the first air resistance body 3. The deflection leads to an intense transverse momentum exchange and thus to the desired effect. The pointed end of the air resistance bodies 3, 4 prevents a "stagnation area," which leads to a great pressure loss, from developing in the wake after the deflection at the blunt end of the air resistance bodies 3, 4. The pressure loss due to the deflection of the flow at the respective blunt end of the body can be prevented from occurring by providing a chamfer or a rounding and, following the base of the second air resistance body 4, a cylindrical section, which passes continuously over into a rounded truncated cone.

The air resistance bodies 3, 4, which are preferably made of plastic according to the injection molding process, are fixed, e.g., by pin-shaped fastening means in the flow channel 1 and mechanically protect the measuring transducer or measuring transducers 5 against effects from the outside and thus they also prevent condensate droplets, sputum or particles from interfering with the measuring function by impinging directly. Another advantage of the present invention is that the free flow cross section does not decrease during clinical use, unlike in the case of screens, whose meshes may become clogged by sputum or condensate droplets. As a result, the pressure loss, the respiratory flow resistance and the uniformization of the properties do not change, either.

The respiratory flow sensor has a standardized outer cone 8 on both apparatus-side legs 7. It is ensured as a result that all tube adapters can be used by the user. The patient-side end P is also provided with a standardized outer cone 9, so that a breathing mask can be connected to it. A collar 10 prevents the respiratory flow sensor from being pushed too far into the mask. The inner side of the patient-side end P is designed such that the connector of an endotracheal catheter 11 can be introduced. However, the sealing is performed by means of a seal 12 rather than by means of a cone, so that the connector can be pushed up to a stop collar 13. A gap, whose width may vary considerably because of the tolerances of the cone, is prevented as a result from being formed between the stop collar and the connector.

The measured signal is preferably led out in parallel to the sensor axis. It is guaranteed as a result that only weak lateral forces and bending moments will be applied to the measuring transducer 5. A great lever is formed due to cables and plugs in the case of perpendicular lead-out. As a result, the measuring transducer 5 may be torn out of its seating in the worst case. In addition, the measuring line can be led without loops to the respiration tubes and from there together with the respiration tubes in the case of parallel lead-out. Handling is improved as a result.

The solution developed for the special requirements has the following form: The flow channel 1 narrows from both ends to the measuring cross section 2 in the middle with a section of constant internal diameter. A first air resistance body 3 in the form of a cone pointing toward the measuring transducer 5, in which the edge between the base and the jacket surface is provided with a 45° chamfer, is located on the patient side P. This body shape causes the flow profile of the exhaled respiratory flow in the measuring cross section 2 to be extensively independent from the diameter and the position of the endotracheal catheter 11 being used and prevents the pressure loss through the body from becoming too high. The cone protrudes into the connector of the endotracheal catheter 11. As a result, a partial volume of the connection is already used for uniformization and the functional dead volume is thus reduced.

A second air resistance body 4, which is composed of a cone pointing toward the measuring transducer 5, a cylinder and a truncated cone, is located on the side away from the patient. The covering surface of the truncated cone is additionally rounded. This body ensures that asymmetries in the flow profile of the inhaled gas volume flow, which are caused by the curvature of the respiration tube, are made uniform. Together with the wall of the flow channel 1, the cylindrical part forms an annular gap, which prevents turbulent whirls, which are generated at sharp edges in the Y-piece, from reaching the measuring cross section 2 and from distorting the measurement result, especially in the case of a simple rinsing flow. Together with the cylindrical part, the rounding on the covering surface ensures a gradual deflection of the flow and thus a low pressure loss. The maximum diameter of the two air resistance bodies 3 and 4 is 5.5 mm on one side and 5.4 mm on the other side in the example, the internal diameter of the measuring cross section 2 is 9 mm, and its length is 10 mm.

Figure 2:
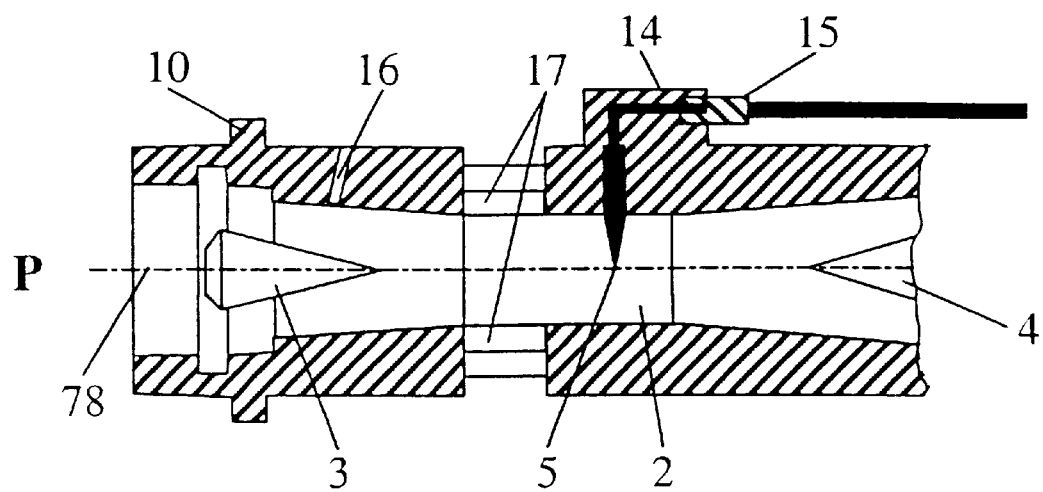

According to the detail in FIG. 2, the sleeve 14 is arranged such that the plug 15, via which the measured signal is led out, extends in parallel to the central longitudinal axis 78 of the flow channel 1. It points in the direction of the movable legs 7 of the Y-piece.

The entire respiratory flow sensor may be manufactured as an injection-molded part from a heat-resistant plastic, so that it can be autoclaved. The two air resistance bodies 3, 4 for making the flow uniform are advantageously manufactured as separate parts and are bonded to the sensor housing.

A breathing gas sampling channel 16 for drawing off breathing gas for a gas analysis may be integrated in the sensor housing. The gas composition affects the measured value by affecting the density, the viscosity and the thermal conductivity in the case of platinum hot wires. The electric signal measured with the hot wire is a function of these variables in the case of a fixed flow. These variables are determined from the gas analysis and are taken into account during the determination of the flow. The proposed integration of the breathing gas sampling channel 16 within the sensor housing is particularly advantageous because it requires no additional plug-in part in the respiration system and consequently no additional functional dead space.

In addition, the sensor housing is optionally equipped with optical windows 17, so that radiation can be passed through the breathing gas by means of a suitable measuring apparatus for infrared spectroscopy and the gas composition can be measured directly in the main stream. Such measuring apparatuses have been known from $CO_2$ measurement and are suitable for the complete gas analysis. The integration of these optional elements in the sensor housing between the first air resistance body 3 on the patient side P and the measuring transducer 5 is advantageous, because good mixing is also achieved due to the uniformization of the flow.

A respiratory flow sensor for obtaining and evaluating the medically relevant information for the breathing gas, namely, the gas volume flow and the gas composition, is obtained by the combination of the respiratory flow sensor with a breathing gas sampling channel 16 and optical windows 17, which combination is described in connection with FIG. 2. Identical components in FIGS. 1 and 2 are designated by the same reference numbers.

While specific embodiments of the invention have been shown and described in detail to illustrate the application of the principles of the invention, it will be understood that the invention may be embodied otherwise without departing from such principles.

What is claimed is:

1. A respiratory flow sensor, comprising:
   a flow channel;
   a measuring transducer in said flow channel, said measuring transducer for measuring breathing gas volume flow;
   an air resistance body in said flow channel, said air resistance body having a blunt end and having an opposite pointed end, said air resistance body being arranged between said measuring transducer and a patient-side end of the respiratory flow sensor, said pointed end of said first air resistance body pointing toward said measuring transducer; and
   a second air resistance body with a pointed end, said second air resistance body being arranged between said measuring transducer and an end of the respiratory flow sensor which end is away from the patient, wherein second air resistance body pointed end also points toward said measuring transducer.

2. A respiratory flow sensor in accordance with claim 1, wherein the respiratory flow sensor is made in one piece with a patient adapter with two legs, said two legs being pivotable around an axis of rotation and said axis of rotation is arranged at right angles to a central longitudinal axis of said flow channel.

3. A respiratory flow sensor in accordance with claim 2, wherein the respiratory flow sensor has a T-shaped adapter connecting the flow channel to the legs.

4. A respiratory flow sensor in accordance with claim 1, wherein said flow channel narrows from both ends to a region of said measuring transducer.

5. A respiratory flow sensor in accordance with claim 1, wherein said measuring transducer sends a measured signal that is proportional to the breathing gas volume flow flowing through said flow channel.

6. A respiratory flow sensor in accordance with claim 1, wherein said measuring transducer is one of an ultrasonic measuring transducer, a hot wire measuring transducer or a differential pressure measuring transducer with or without movable diaphragms.

7. A respiratory flow sensor in accordance with claim 1, wherein said air resistance body has a rotationally symmetrical design with a symmetry axis substantially coinciding with a central longitudinal axis of said flow channel.

8. A respiratory flow sensor in accordance with claim 1, wherein each of said air resistance body and said second air resistance body have a rotationally symmetrical design with a symmetry axis substantially coinciding with a central longitudinal axis of said flow channel.

9. A respiratory flow sensor in accordance with claim 1, wherein said blunt end of said air resistance body has a base in the form of one of a circle or a regular polygon.

10. A respiratory flow sensor in accordance with claim 9, wherein said air resistance body has a base and a jacket surface with a chamfer or a rounding provided between said base and a jacket surface.

11. A respiratory flow sensor in accordance with claim 1, wherein following the pointed end, said second air resistance body has a cylindrical course with a closure joining it in the form of a rounded truncated cone.

12. A respiratory flow sensor in accordance with claim 1, further comprising: a plug extending essentially in parallel to the central longitudinal axis of the flow channel, said plug leading out the measured signals of the measuring transducer.

13. A respiratory flow sensor in accordance with claim 1, wherein a distance between said measuring transducer and said air resistance body is greater than or equal to a diameter of said air resistance body.

14. A respiratory flow sensor in accordance with claim 1, wherein a distance between said measuring transducer and said air resistance body and a distance between said measuring transducer and said second air resistance body is greater than or equal to a diameter of the respective said air resistance body.

15. A respiratory flow sensor in accordance with claim 1, wherein said flow channel includes optical windows arranged opposite and in parallel to a central longitudinal axis far spectroscopic radiation through the flow channel and a said breathing gas sampling channel.

16. A respiratory flow sensor, comprising:
   a flow channel having a patient side end and an opposite end connected to one or both of an intake and discharge end, said flow channel having a flow direction between said patient side and said opposite end;
   a measuring transducer in said flow channel between said patient side end and said opposite intake and discharge end, said measuring transducer for measuring breathing gas volume flow;

an air resistance body in said flow channel and spaced apart from said measuring transducer with respect to said flow direction, said air resistance body having a blunt end and having an opposite pointed end, said air resistance body being arranged between said measuring transducer and said patient-side end of the respiratory flow sensor, said pointed end of said first air resistance body pointing toward said measuring transducer.

17. A respiratory flow sensor in accordance with claim 16, further comprising:

a second air resistance body with a pointed end, said second air resistance body being arranged between said measuring transducer and said opposite end, wherein said second air resistance body pointed end also points toward said measuring transducer.

18. A respiratory flow sensor in accordance with claim 17, wherein the respiratory flow sensor is made in one piece with a patient adapter with two legs, said two legs being pivotable around an axis of rotation and said axis of rotation is arranged at right angles to a central longitudinal axis of said flow channel.

19. A respiratory flow sensor in accordance with claim 16, wherein said air resistance body has a rotationally symmetrical design with a symmetry axis substantially coinciding with a central longitudinal axis of said flow channel.

20. A respiratory flow sensor, comprising:

a flow channel having a patient side end and an opposite intake and discharge end;

a measuring transducer in said flow channel between said patient side end and said opposite intake and discharge end, said measuring transducer for measuring breathing gas volume flow;

an air resistance body in said flow channel spaced a distance from said measuring transducer along said flow channel, said air resistance body having a blunt end and having an opposite pointed end, said air resistance body being ranged between said measuring transducer and said patient-side end of the respiratory flow sensor, said air resistance body being substantially rotationally symmetrical with a symmetry axis substantially coinciding with a central longitudinal axis of said flow channel and with said pointed end of said first air resistance body pointing toward said measuring transducer.

* * * * *